United States Patent
Gramann

(10) Patent No.: US 9,375,291 B2
(45) Date of Patent: Jun. 28, 2016

(54) DEVICE FOR DISPENSING A DENTAL MATERIAL

(76) Inventor: Jens Gramann, Gräfelfing (DE)

( * ) Notice: Subject to any disclaimer, the term of this patent is extended or adjusted under 35 U.S.C. 154(b) by 19 days.

(21) Appl. No.: 13/390,269

(22) PCT Filed: Aug. 25, 2010

(86) PCT No.: PCT/US2010/046664
§ 371 (c)(1),
(2), (4) Date: Feb. 13, 2012

(87) PCT Pub. No.: WO2011/025831
PCT Pub. Date: Mar. 3, 2011

(65) Prior Publication Data
US 2012/0148980 A1 Jun. 14, 2012

(30) Foreign Application Priority Data
Aug. 28, 2009 (GB) .................................. 0915002.0

(51) Int. Cl.
*A61C 5/04* (2006.01)
*A61C 5/06* (2006.01)
*B05C 17/005* (2006.01)
*B05C 17/01* (2006.01)

(52) U.S. Cl.
CPC ............... *A61C 5/062* (2013.01); *A61C 5/064* (2013.01); *B05C 17/00553* (2013.01); *B05C 17/0103* (2013.01); *B05C 17/0133* (2013.01)

(58) Field of Classification Search
USPC ............. 433/80–90, 215; 604/155, 152, 154; 222/135–138, 326, 333, 386, 390; 135/80–90, 215
See application file for complete search history.

(56) References Cited

U.S. PATENT DOCUMENTS

| 1,328,567 | A | * | 1/1920 | Jones | ........................... 222/390 |
| 3,521,356 | A | | 7/1970 | Newman | |
| 4,180,187 | A | | 12/1979 | Ben-Haim | |
| 4,322,022 | A | | 3/1982 | Bergman | |
| 5,207,357 | A | | 5/1993 | Aronie | |
| 5,286,105 | A | | 2/1994 | Herold | |

(Continued)

FOREIGN PATENT DOCUMENTS

| CA | 2 638 859 | 8/2008 |
| EP | 1 892 045 | 8/2007 |

(Continued)

OTHER PUBLICATIONS

International Search Report for International Application No. PCT/US2010/046664, dated Nov. 17, 2010.

*Primary Examiner* — Yogesh Patel
(74) *Attorney, Agent, or Firm* — Nicole J. Einerson

(57) ABSTRACT

A dispensing device comprises a compartment for receiving a dental material, a piston for extruding the material from the compartment and a spindle drive for moving the piston and the compartment relative to one another. The spindle drive comprises a spindle and a link which are adapted for disengageable engagement with one another, wherein the spindle and the link are operable relative to each other between an engaged position in which the link and the spindle are engaged with one another, and a disengaged position in which the spindle and the link are disengaged from one another. The device may be relatively robust and inexpensive to manufacture, and may facilitate preparation of dental materials for use.

18 Claims, 12 Drawing Sheets

(56) References Cited

U.S. PATENT DOCUMENTS

| | | | |
|---|---|---|---|
| 5,860,739 A | 1/1999 | Cannon | |
| 6,168,052 B1 | 1/2001 | Keller | |
| 6,428,750 B1 * | 8/2002 | Rainin et al. | 422/516 |
| 6,794,612 B2 * | 9/2004 | Furtwangler | B05C 17/00533 219/227 |
| 7,980,428 B2 | 7/2011 | Beckett | |
| 2010/0143864 A1 * | 6/2010 | An | 433/89 |

FOREIGN PATENT DOCUMENTS

| | | |
|---|---|---|
| JP | 57-000033 Y | 1/1982 |
| KR | 100 906 825 | 7/2009 |
| WO | WO 2006/106215 | 10/2006 |

\* cited by examiner

DEVICE FOR DISPENSING A DENTAL MATERIAL

CROSS REFERENCE TO RELATED APPLICATIONS

This application is a national stage filing under 35 U.S.C. 371 of PCT/US2010/046664, filed Aug. 25, 2010, which claims priority to Great Britain Patent Application No. 0915002.0, filed Aug. 28, 2009, the disclosures of which are incorporated by reference in their entirety herein.

FIELD OF THE INVENTION

The invention relates to a device for dispensing a dental material. In particular the invention relates to a device having a spindle drive for moving a piston and a compartment for the material relative to one another.

BACKGROUND ART

In dentistry a variety of devices are available which allow for preparation and/or application of dental materials in a dentist's practice. In particular for preparation of materials that are typically used in larger amounts, like for example dental impression materials, devices have been developed that provide for automatic dispensing from packages and/or for mixing of such materials. An exemplary device for mixing and dispensing a dental impression material is for example available under the designation 3M™ ESPE™ Pentamix™ from 3M ESPE AG, Germany. Typically such a device allows for two material components to be simultaneously supplied from a package through a mixer where they are mixed. Often the devices provide for continuously extruding the components through a mixer, where the components are mixed as the components flow through the mixer and released from an outlet.

The devices further typically have a motor driven piston for extruding the material from a container. Some motor driven devices implement drive concepts providing for driving the piston at different modes. For example in a first mode the material may be dispensed by slow movement of the piston at high forces, and in a second mode the pistons may be movable fast for enabling quick service operations, like material exchange or cleaning, for example.

For example U.S. Pat. No. 5,286,105 A discloses a device for mixing and dispensing two-component materials. The device has two pistons which can be advanced in cartridges by an electric motor via a magnetic clutch. When the motor is switched off and the clutch is disengaged, the pistons may be manually retracted and re-advanced by a hand wheel relatively quickly, for example for exchanging the cartridges in the device.

Further U.S. Pat. No. 6,168,052 B1 discloses an electrically driven dispensing appliance acting via drive screws on thrust plates for dispensing material from cartridges. The drive screws are axially stationary and act on the thrust plates. The electric drive comprises a first gear motor for a drive under high load during advance and relief, and a second motor for the drive under lower load during the retracting and fast advance motions. During advance and relief the drive screws are coupled to the first gear motor by a coupling, and during retracting and fast advance motions the drive screws are decoupled from the first gear motor but driven by the second gear motor.

Although available mixing and dispensing devices provide certain advantages there is still a need for a relatively inexpensive device, but which is operable relatively conveniently. Further a desirable dispensing device preferably is relatively reliable, and compact in design.

SUMMARY OF THE INVENTION

The invention is directed to a device for dispensing a dental material. The device comprises at least one compartment for receiving the dental material, at least one piston for extruding the dental material from the compartment and a spindle drive for moving the piston and the compartment relative to one another. The spindle drive comprises a spindle and a link which are adapted for disengageable engagement with one another, wherein the spindle and the link are operable relative to each other between an engaged position in which the link and the spindle are engaged with one another, and a disengaged position in which the spindle and the link are disengaged from one another.

The invention preferably allows the piston to be moved at relatively high forces via the spindle drive to dispense material when the link and the spindle are in the engaged position. Further the device preferably allows the link and the spindle to be disengaged for enabling fast retraction and repositioning of the piston. The invention may be advantageous in that it may enable a relatively unsophisticated design of the device. In particular the device may not need a gear box, or may have only a relatively simple gear box for transforming a circular motion of a motor into a linear displacement of the piston. The invention may also be advantageous in that it allows similar designs for different devices providing different forces and/or speeds for moving the piston. Further the invention may allow providing different mixing ratios with similarly designed devices. Thus the invention may provide for a device design that is relatively flexible for adaptation to different applications. Therefore costs in manufacturing may also be saved. The invention may also be advantageous in that it may provide for devices that are relatively reliable and robust.

In one embodiment the link and the spindle in the engaged position are rotatable relative to each other about a rotation axis, and adapted such that a rotation causes the spindle and the link to displace relative to each other along the rotation axis, or axially to the rotation axis. The rotation axis may for example correspond to a longitudinal axis of the spindle, or may be generally parallel to the longitudinal axis of the spindle. The displacement between the spindle and the link preferably provides for a displacement between the piston and the compartment for extruding the dental material. Thus the spindle drive in the engaged position may be used to advance the piston for dispensing material from the compartment.

In another embodiment the piston is mechanically connected with either the spindle or the link. Thus the displacement between the spindle and the link preferably substantially corresponds to the displacement between the piston and the compartment. Therefore no further speed transformation may be required between the spindle drive and the piston.

In one embodiment the spindle is threaded and the link has an engagement structure for engaging the spindle thread. The engagement structure may be a thread or at least a partial thread. Other structures suitable for positively engaging the spindle thread may be used as appropriate, like for example one or more pins.

In another embodiment the link comprises a nut carrying the engagement structure. The nut and the spindle are preferably movable relative to each other in a direction generally perpendicular to the rotation axis (or generally perpendicular to the longitudinal axis of the spindle) for operating the spindle and the link toward the engaged or the disengaged position. Thus the link and the spindle can be engaged and disengaged by relative movement between one another in a direction generally perpendicular to the rotation axis. Therefore the spindle and the link may be axially displaceable relative to one another for displacing the piston, and additionally the nut and the spindle may be laterally movable relative to one another for engagement and disengagement of the link and the spindle.

The engagement structure is preferably arranged at a section of the nut which only partially surrounds the spindle. Therefore the spindle and the nut can be joined for engagement and separated for disengagement with one another.

In a further embodiment the relative movement between the spindle and the nut is provided by the nut being pivotable relative to the spindle about a pivot axis. The pivot axis preferably extends generally transverse to the rotation axis. Thus the nut and the link are preferably not only movable about the rotation axis relative to one another, but also in a direction transverse thereto. The skilled person will recognize that a transverse direction may include directions that are inclined to a certain extent to a normal on the rotation axis without departing from the invention.

In one embodiment the nut is further adapted such that the engagement structure is radially offset from the pivot axis. The nut further is preferably adapted and arranged such that the engagement structure moves generally perpendicular to the rotation axis of the spindle during operation of the spindle and the nut from the engaged toward the disengaged position. Therefore the direction of the relative movement between the spindle and the nut during engaging and disengaging may have a lateral component perpendicular to the rotation axis and a further smaller axial component in a direction parallel to the rotation axis. Thus a smooth engagement and disengagement may be achieved. The engagement structure may further be omitted in areas in which the axial component would dominate over the lateral component. Thereby it may be avoided that the engagement structure and the spindle thread interlock and prevent pivoting of the nut. In an example the nut, in the engaged position, has a first end adjacent the position of pivot axis and an opposite second end radially offset from the pivot axis in a direction along the rotation axis. Therefore the pivot axis may be located closer to the first than to the second end. The engagement structure is preferably arranged adjacent the second end and is omitted or reduced adjacent the first end.

In another embodiment the pivot axis is arranged outside an outer perimeter or outside the effective diameter of the spindle thread. The engagement structure may be arranged in a radius from the pivot axis, with the radius being greater than the distance between the pivot axis and the outer perimeter or outside the effective diameter of the spindle thread. Such a configuration may cause the nut being urged toward the engaged position by forces resulting from dispensing material.

Therefore a self-locking effect may be provided which maintains the link and spindle engaged even when loaded by relatively high forces. Thus a relative reliable operation of the device may be achieved.

In one embodiment the spindle and the nut are urged in the engaged or in the disengaged position by spring load. Therefore the nut may be urged toward a default position by a spring, and may be operable toward an alternative position against spring load. For example in one embodiment the nut is urged toward the engaged position by default. When the device is used for dispensing material the self-locking effect may additionally support keeping the link and the spindle engaged, so that material may be reliably dispensed from the device. In this example the nut may be operable towards the disengaged position for fast movement of the piston, for example by a user.

In a further embodiment the nut is connected to an actuator. The actuator preferably allows for moving the nut toward the disengaged position against spring load. Therefore the link and the spindle preferably reengage when for example a user releases the actuator. Thus the device may by default be prepared to dispense material, but may be temporarily operated for quick positioning of the piston.

In another embodiment the device has a cam which is operable for retaining or locking the nut in the engaged position against the spring load, and for releasing the nut so that it can move toward the disengaged position by spring load. In this embodiment the cam may retain or lock the link and the spindle engaged with one another when the device is used for dispensing material. The device may be adapted to automatically cause the cam to release the nut when dispensing is stopped so that the link and the spindle automatically disengage. This may allow pressure built up in the compartment to relieve upon stopping dispensing. Thus afterflow of the material may be prevented.

In a further embodiment the nut is guided for a parallel motion in a direction generally lateral to the rotation axis of the spindle. Such guidance at least in the engaged position of the nut and the spindle is preferably provided in a guiding direction that is between a parallel and a perpendicular direction relative to the rotation axis of the spindle (the guiding direction thus preferably being non-parallel and non-perpendicular to the rotation axis of the spindle). Further the guiding direction is preferably oriented generally parallel to a flank angle of the spindle thread. The flank angle for the purpose of this specification is defined between the rotation axis and a surface of the flank of the thread in a plane aligned with the rotation axis. The flank angle may be for example within a range of about 70 to about 85 degrees, and preferably about 85 degrees.

In a further embodiment the guiding direction may be smaller than the flank angle. In this embodiment then operation of the spindle drive in one displacement direction preferably causes the nut to be urged toward the spindle. Thus a self-maintained engagement of the nut and the spindle in one displacement direction of the nut and the spindle relative to one another may be provided.

In another embodiment the link and the nut are guided in the guiding direction by at least one of a linear guide, and a parallelogram guide. The linear guide may comprise a roller guide, and the parallelogram guide may comprise at least one lever which connects the link and the nut pivotally.

In one embodiment the link comprises a pitch finder for aligning the threads of the spindle and the nut relative to each other. The pitch finder is preferably adapted for resiliently snap between flanks, for example between opposing sides of two adjacent flanks, of the spindle thread. This may help to pre-position the spindle and the link, when disengaged, relative to one another, and allow for smooth engagement of the link and the spindle when pre-positioned.

In one embodiment the device may have at least one plunger carrying the piston. In one embodiment the spindle is axially movable in the device, and the link is axially fixed relative to the device. Therefore the spindle may form at least a part of the plunger.

In another embodiment the spindle is axially stationary in the device, and the link is axially movable in the device. In this embodiment the piston may be mechanically connected with the link, for example via a plunger.

In one embodiment the device has two plungers, two compartments and two pistons. Such a device preferably is further adapted to mix components received in the compartments to form the dental material. The device may further comprise two spindle drives each comprising a spindle and a link. The two links may be rotatably interconnected so that rotation of one causes rotation of the other one.

In one embodiment the links each comprise a gear rim which are disengaged from each other, but each engage a gear wheel. Thus the links are preferably rotatably interconnected for rotation in the same direction. The gear rims and the pitches of the spindles are preferably selected such that the spindles displace axially generally synchronously when the gear wheel drives the links. For example the gear rims may have the same amount of teeth and the spindles may have the same pitches. The skilled person will recognize that a similar effect can be achieved by gear rims having different amounts of teeth and spindles having different pitches, but which in combination compensate to provide for a synchronous displacement. Further the skilled person will recognize that according to a reversed principle the spindles each may have a gear rim that engages with a gear wheel for rotatably interconnecting the spindles. In this embodiment the gear rims and the pitches of the spindles can be likewise selected to cause a synchronous displacement of the links parallel to the rotation axis of the spindles. The components of the dental material may therefore be generally synchronously advanced, and the mixing ration of the components may be predetermined by the cross-section of the compartments. The compartments therefore may empty generally synchronously so that the components may always be replaced in a set. This may save time for replacing individual compartments.

Nevertheless the device may further be adapted to asynchronously advance the components. This may allow for mixing the components a mixing ratio that is independent from the cross-section of the compartment. Therefore such a device may allow mixing materials at a ratio defined by the device rather than at a ration predetermined by the cross-section of the compartment. Accordingly the device may be adapted for retrofitting with spindle drives that provide asynchronous advancement of the components at certain different ratios.

In one embodiment the device has an electric motor for driving the spindle drive(s). The motor may be an electric DC motor, for example, or any other suitable motor. The device may further have a hand wheel which is adapted for driving or displacing the piston when the spindle drive is in the disengaged position. For example the hand wheel may be connected to a chain, belt or rod which converts the rotation of the hand wheel into a displacement of the piston. Thus a fast manual movement of the piston maybe enabled. In the engaged position of the spindle drive the hand wheel may be driven via the spindle drive. This may indicate a user that material is advanced in the device. The piston is typically blocked against manual displacement by the hand wheel when the spindle drive is in the engaged position. Therefore unintentional operating the hand wheel during dispensation may not adversely affect the dispensation, and thus an additional coupling for decoupling the hand wheel from the spindle drive may be saved.

DETAILED DESCRIPTION OF THE INVENTION

Figure 1:
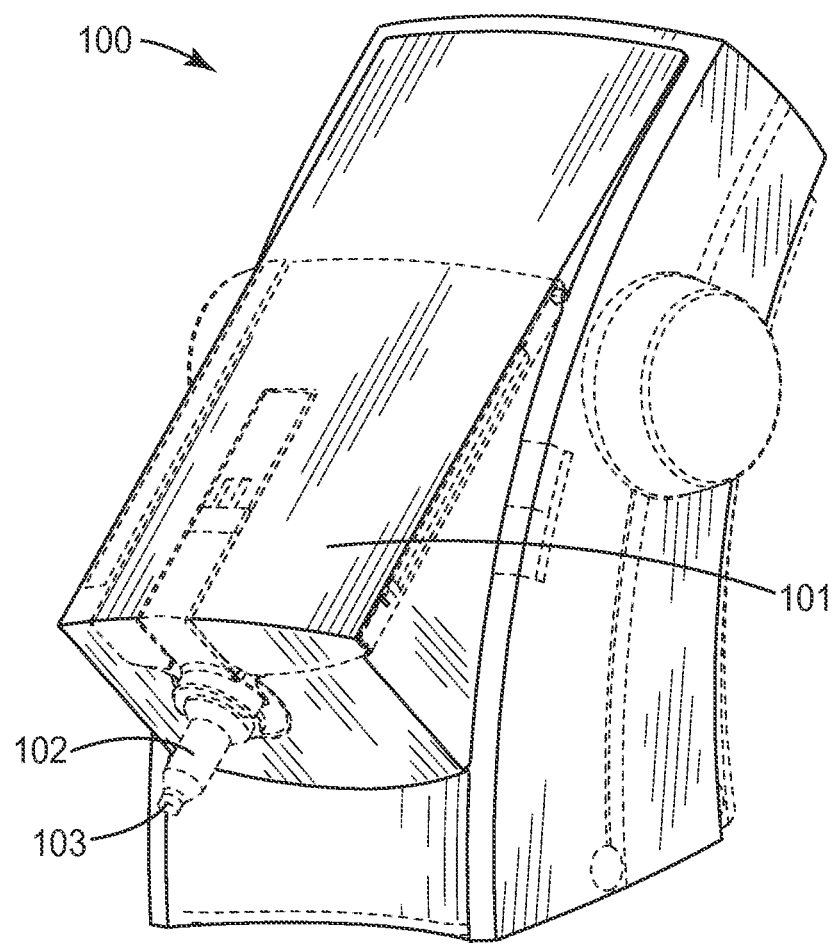
FIG. 1 is a perspective view of a device for mixing and dispensing a dental material.

FIG. 1 shows a device 100 for dispensing dental materials. The device 100 comprises a receptacle 101 for receiving the material in preferably the form of two separate components, and a mixer 102 for mixing the components. The material components are preferably contained in separate compartments (not shown) from which the components can be extruded into the mixer. The mixer 102 is connected with the compartments such that the individual components can be advanced into a mixing chamber of the mixer where the components can be mixed, for example by help of a rotating mixing rotor. The mixture can exit through an outlet 103 of the mixer 120. The device shown may be used to mix and dispense a hardenable dental impression material, for example. Mixed dental impression material may for example be used to fill a dental tray which is then placed into a patient's mouth for taking a dental impression. The mixer 102 of the device shown is replaceably attached at the device 100. Therefore when the mixed material hardens and thus blocks the mixer the used mixer may be replaced by an unused mixer for the next use of the device. A similar device is available under the designation 3M™ ESPE™ Pentamix™ from 3M ESPE AG, Germany.

Figure 2B:
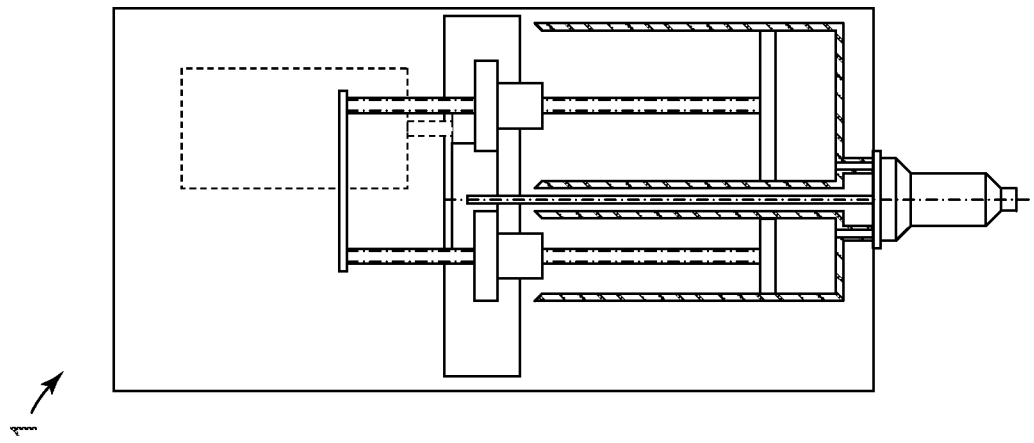
FIG. 2a, 2b are schematic views of a device at different operational stages according to an embodiment of the invention.
Figure 2A:
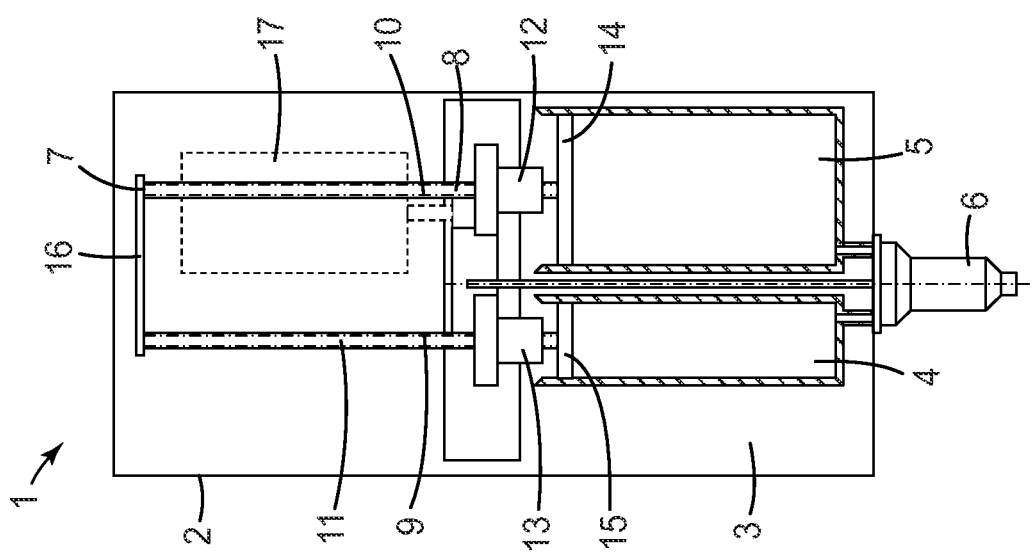

FIGS. 2a and 2b show a device 1 of the invention in more detail. The device 1 has a housing 2 which has a receptacle 3 in which a first compartment 4 and a second compartment 5 are received. FIG. 2a shows the device 1 in an initial position, for example when the compartments are still substantially full of material components, and FIG. 2b shows the device 1 at a different operational stage, for example when a part of the compartments is extruded from the compartments.

A mixer 6 is received on outlets of the compartments 4, 5. The compartments 4, 5 are replaceable in the device, thus allowing for example the use different types of materials in the same device, or the exchange of empty compartments by full ones. In the example shown the mixer 6 is attached to the compartments 4, 5 such that the mixer 6 and the compartments 4, 5 form a unit that can be replaced in one. Further the mixer may be replaced at the compartments so that an unused mixer may be used for each new use of the device. The skilled person will recognize that the mixer may not necessarily form a unit with the compartments, but may for example remain at the device when the compartment is removed and may be connectable to new compartments inserted in the device.

The device 1 further has a plunger assembly 7 which in the example is arranged in the housing 2. Therefore the plunger assembly may be protected from environmental substances, like disinfectants or dirt. The plunger assembly 7 comprises a first spindle drive 8 and a second spindle drive 9. The first and second spindle drives 8, 9 each have a first spindle 10 and a second spindle 11, as well as a first link 12 and a second link 13, respectively. In the example shown the spindles 10, 11 are axially movable. In particular the spindles 10, 11 are drivable axially by rotation of the links 12, 13. The links 12, 13 in the example are axially fixed in the device. Therefore the links are rotatable but axially fixed, and the spindles are axially movable but rotationally fixed (or secured against rotation). In a preferred embodiment each of the spindles 10, 11 are threaded and the corresponding links 12, 13 have a nut (not shown in detail in this figure) each having an appropriate engagement structure. An appropriate engagement structure may for example comprise one or more pins or at least part of a thread, to engage the spindle. Thus each of the links may cause the corresponding spindle to axially move when the link is rotated in an engaged cooperation with the spindle.

In the example the spindles 10, 11 form at least a part of plungers which at their front end carry pistons 14, 15. Therefore the pistons 14, 15 may be advanced by the axially moving spindles for extruding the material components. The device of the embodiment shown is preferably adapted such that the spindles are advanced generally simultaneously. Therefore the spindles may be connected at their rear ends by a connection bar 16. The connection bar may help to guide the spindles generally parallel to one another. An electric motor 17 is arranged in the device to drive the spindles via the links 12, 13, and in addition optionally a mixer shaft (not shown) for driving the mixing rotor in the mixer. A more detailed description about the drive mechanism for the spindle and the mixer shaft is provided further below.

Figure 3A:
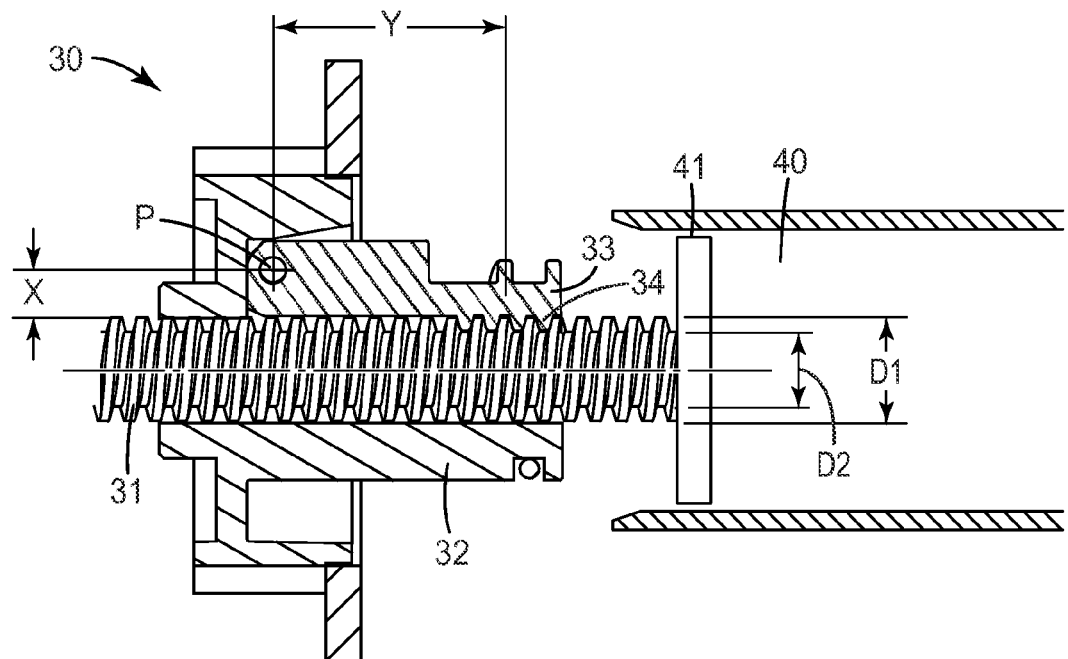
FIG. 3a, 3b are cross-sectional views of a spindle drive at different operational stages according to an embodiment of the invention.
Figure 3B:
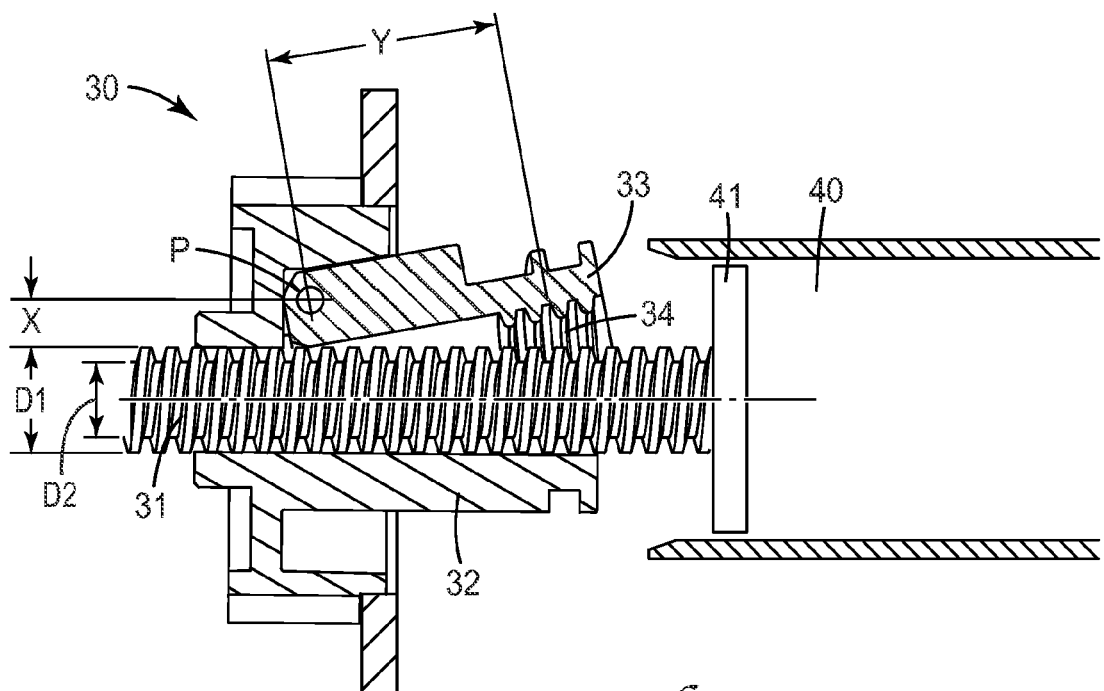

FIGS. 3a and 3b are cross-sectional views showing a spindle drive 30 according to an embodiment of the invention at different operational stages. Further a compartment 40 is shown in which a piston 41 is movably arranged for dispensing material from the compartment 40. The spindle drive 30 has a threaded spindle 31 which cooperates with a link 32. The spindle 31 and the link 32 are adapted for disengageable engagement with one another. In particular the link 32 has a threaded nut 33 which is movable relative to the spindle between a position in which the nut 33 and the spindle 31 are engaged with one another (FIG. 3a) and a position in which the nut 33 and the spindle 31 are disengaged from one another (FIG. 3b).

In the engaged position shown in FIG. 3a the spindle drive can be used to advance the piston for extruding material. In the example the link 32 may be rotated to advance the spindle 31 in a forward direction toward the compartment 40. The spindle drive is preferably adapted to transmit relatively high forces during advancing the piston. For example the pitch of the thread may be selected such that the spindle moves relatively slowly although the link is driven at a relatively high speed. Therefore the spindle drive preferably increases forces provided by a drive for driving the spindle drive to higher forces for advancing the piston.

In FIG. 3b the nut 33 is shown in the disengaged position. In this position the link and the spindle are freely movable relative to one another in an axial direction of the spindle, for example without relative rotation between the link 32 and the spindle 31. Thus the disengaged position allows a free displacement of the piston. For example in the disengaged position a user may quickly retract the piston from the compartment for exchanging the compartment by a new one. Further the user may quickly reposition the piston towards the new compartments so that substantially instantly after switching to the engaged position new material can be dispensed.

In the disengaged position the piston may be driven manually or by a positioning drive. Therefore the device of the invention in the engaged position of the spindle drive may provide for the piston to be drivable at relatively high forces and at relatively slow speed. Further the device of the invention in the disengaged position of the spindle drive may provide for the piston to be drivable at relatively high speed whereby relatively low forces may be involved.

The embodiment shown in FIG. 3a and FIG. 3b may generally be used in combination with other embodiments described in this specification and is therefore described in more detail in the following. The nut 33 is pivotally connected with the link 32. The pivot axis P is oriented generally transverse to the axial direction of the spindle (about perpendicularly to the plane of the figure). Therefore the threads of the spindle 31 and the nut 33 can be brought in engagement or disengagement with one another by pivoting the nut 33 about the pivot axis P. Thus the spindle and the link are operable relative to each other between an engaged position in which the link and the spindle are engaged with one another, and a disengaged position in which the spindle and the link are disengaged from one another.

The threaded spindle 31 is characterized by an outer thread diameter D1, and an effective diameter D2. The effective diameter of the spindle preferably corresponds to about the medium diameter between a minor thread diameter and the outer thread diameter. The effective diameter D2 of a thread is typically used to define a theoretic force application line for axial forces that may be transmitted between the thread and an appropriate complementary cooperating thread. In the example the pivot axis P is arranged outside the outer thread diameter D1 of the spindle, and in particular outside the effective diameter D2 of the spindle. Therefore an axial force which acts between the spindle and the nut also causes a torque which urges the nut to move about the pivot axis. In the example the nut 33 is further adapted such that the torque when the nut drives the spindle in a forward direction (in a direction toward compartment 40) urges the nut toward the engaged position, but when the nut drives the spindle in an opposite backward direction (in a direction away from compartment 40) urges the nut toward the disengaged position. Because the extent of the torque depends on the transmitted axial force a higher axial force will also cause the nut to be more extensively urged towards one of the engaged or disengaged position. Thus a self-locking function may be provided which keeps the nut engaged with the spindle during the spindle is displaced forwards even when the spindle drive is used to transmit high forces. Further in this way a self-unlocking function may be provided which allows for automatic disengaging the nut from the spindle upon reversing the displacement direction of the spindle to a backward direction.

In the embodiment shown the pivot axis is radially spaced from the effective diameter by a distance X from the effective thread diameter D2. Further the engagement structure 34 of the nut (in the example shown a partial thread) is radially offset by a distance Y from the pivot axis. For determining the distance Y of the engagement structure preferably the center of the structure with respect to its axial extension when engaged with the spindle is used. Thus a leverage may be implemented which transforms an axial force F1 transmitted during axial displacement of the spindle and the nut relative to one another into a radial Force F2 urging the nut radially toward or away from the spindle. The ratio between F2 and F1 thereby corresponds to the ratio between X and Y respectively (F2:F1=X:Y). Preferably Y is greater than X.

Figure 4:
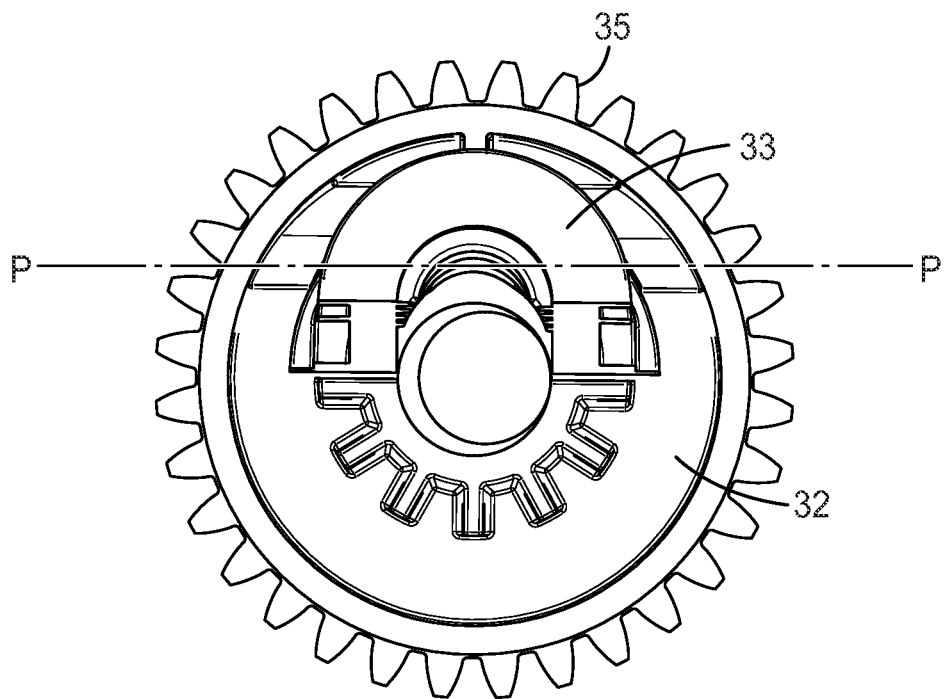
FIG. 4 is a front view of a link for cooperating with a spindle according to an embodiment of the invention.

FIG. 4 is a front view of the link 32 illustrated in FIGS. 3*a*, 3*b* with the nut 33 shown in the disengaged position. Further the position of the pivot axis P is indicated. The link 32 in the example is itself rotatable (around an axis generally perpendicular to the plane of the Figure). The nut 33 is pivotally attached to the link so that a rotation of the link also causes a rotation of the nut. The skilled person will be aware of other solutions in which the nut is drivable and rotatable relative to the link, or in which the link has rotatable and non-rotatable components. In the example the link has a geared rim 35 allowing for the link and thereby the nut to be driven. Also in this regard the skilled person will recognize that other structures than a gear may be likewise used, like a sprocket, a belt pulley, a friction gear or any other appropriate structure allowing for driving the link and/or the nut.

Figure 5:
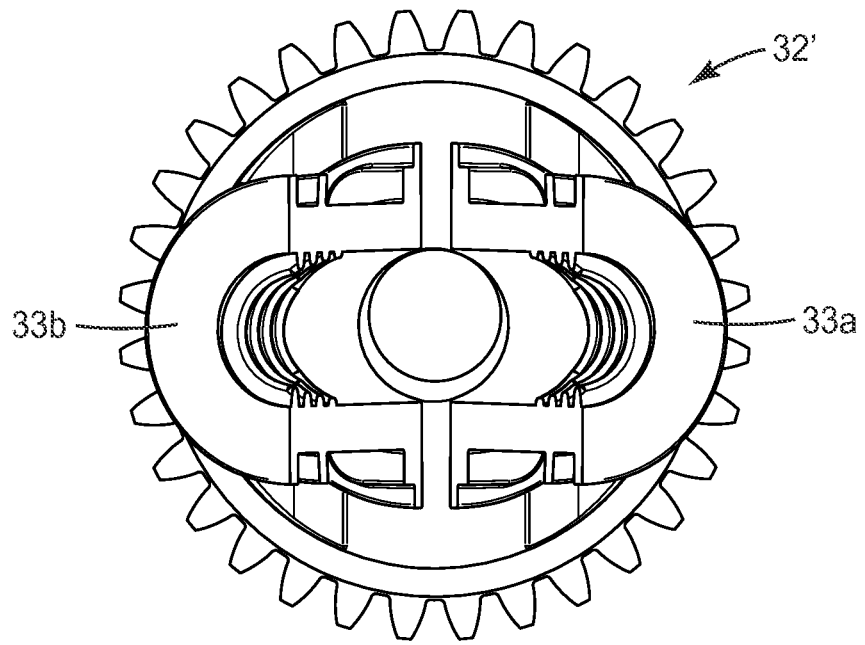
FIG. 5 is a front view of a further link for cooperating with a spindle according to an embodiment of the invention.

FIG. 5 is a front view of a link 32' according to a further embodiment of the invention. The link 32' generally corresponds to the link 32 shown in FIG. 4, but in this example has two nuts 33*a*, 33*b* which are shown in the disengaged position. The two nuts 33*a*, 33*b* may be threaded and may together entirely or generally entirely surround the spindle (not shown) when combined in the closed position. Thus the force transmittable by the link may be increased relative to a link having only one nut.

Figure 6:
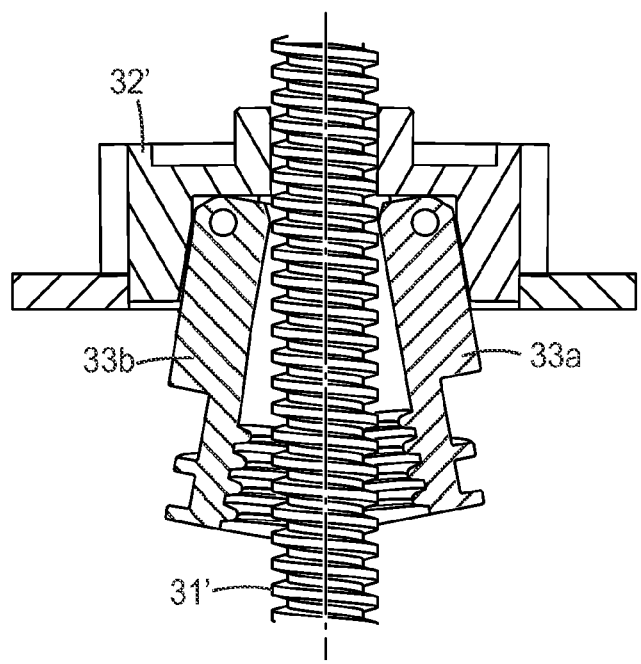
FIG. 6 is cross-sectional view of the spindle drive according to the embodiment shown in FIG. 5.

FIG. 6 illustrates the link 32' in combination with a spindle 31'. The configuration shown generally corresponds to the embodiments shown in FIG. 3*a* and FIG. 3*b*, however differentiates in that the link 32' has two nuts 33*a*, 33*b* instead of one nut.

It will be clear to the person skilled in the art that only one or both of the nuts may be threaded for cooperation with the spindle. Further more than two nuts may be used all or part of which may be threaded.

Figure 7:
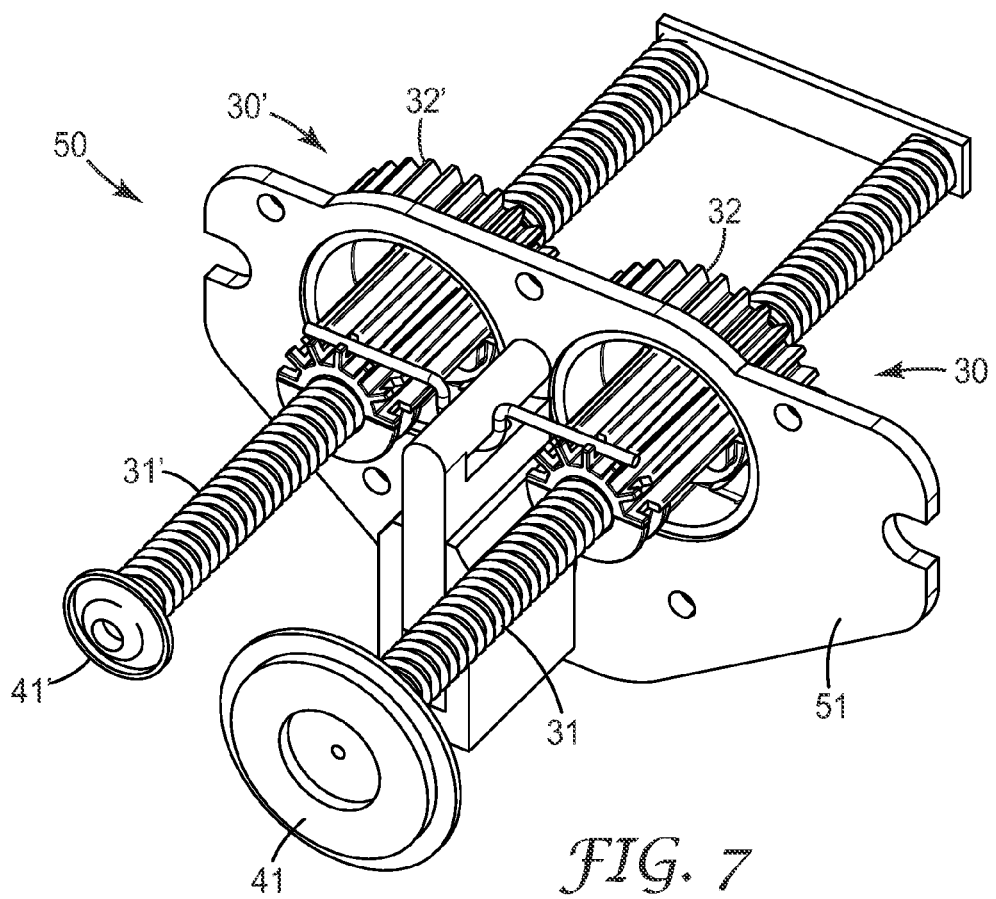
FIG. 7 is a perspective view of an assembly comprising two spindle drives according to an embodiment of the invention.

FIG. 7 shows an assembly 50 which comprises the spindle drive 30 and a second similar spindle drive 30'. The links 32, 32' are arranged on a support 51 which may be mounted fixedly into the device. Therefore the links 32, 32' when rotated cause the spindles 31, 31' to displace axially. The spindles 31, 31' in the example form plungers carrying pistons 41, 41'. In the example shown the spindles 31, 31' have similar pitches so that a synchronous rotation of the links causes the spindles to displace generally synchronously. Thus the pistons 41, 41' are advanced generally synchronously. In this embodiment a desired mixing ratio of the components may be predetermined by the cross-sections of corresponding compartments. For example a mixing ratio which is different from 1:1 may be achieved by different cross-sections of the compartments.

In another embodiment the spindles may have different pitches which may allow for asynchronous displacement of the spindles and therefore for achieving mixing ratios different from 1:1 with compartments having generally equal cross-sections. This may for example be advantageous because the compartments may be manufactured at a uniform size and thus the amount of variants during manufacturing may be reduced. In another embodiment the links may be rotated at different speeds to achieve a similar function. Therefore the same device could be used to dispense material components at different mixing ratios at different operation modes, for example with the operation modes being user selectable. A further embodiment comprises a combination of different pitches and different rotation speeds.

Figure 8:
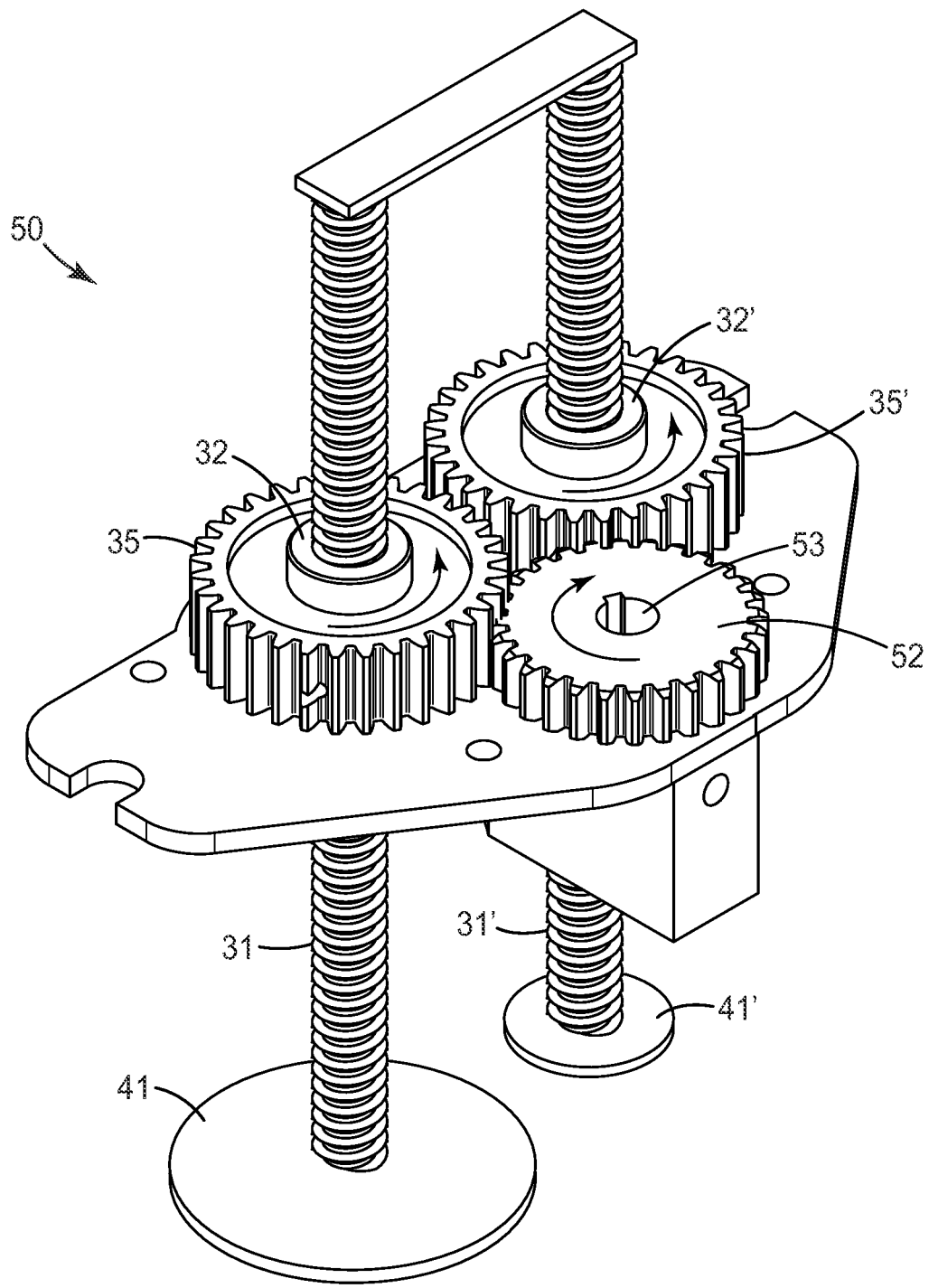
FIG. 8 is a further perspective view of an assembly comprising two spindle drives according to an embodiment of the invention.

FIG. 8 shows the assembly 50 from a different perspective. The assembly 50 has a drive wheel 52 which connects the gear rim 35 of the link 32 and the gear rim 35' of the link 32'. Therefore the links 32, 32' are connected for a rotation in the same direction. Other solutions are possible for a similar connection, like for example a connection of the links via a chain or a gear belt. The drive wheel 52 has a hub 53 which is adapted to engage with a mixer shaft (not shown) for driving a mixer.

The numbers of teeth on the drive wheel and of the gear rims 35, 35' as well as the dimension of the pitches of the spindles 31, 31' are selected to provide in combination for a certain desired relationship between the rotation speed of the mixer shaft and the displacement speed of the spindles 31, 31'/pistons 41, 41'. The rotation speed of the drive shaft may for example correspond to a designed rotation speed of a standard motor. This may make a separate gear box for speed adaptation between the motor and the mixer shaft unnecessary. This rotation speed then is preferably transformed into an appropriate displacement speed suitable for extruding material components from the compartments. Thus the same motor may be used for driving the mixer shaft and the pistons, and a separate motor or an additional gear box may be saved.

Figure 9:
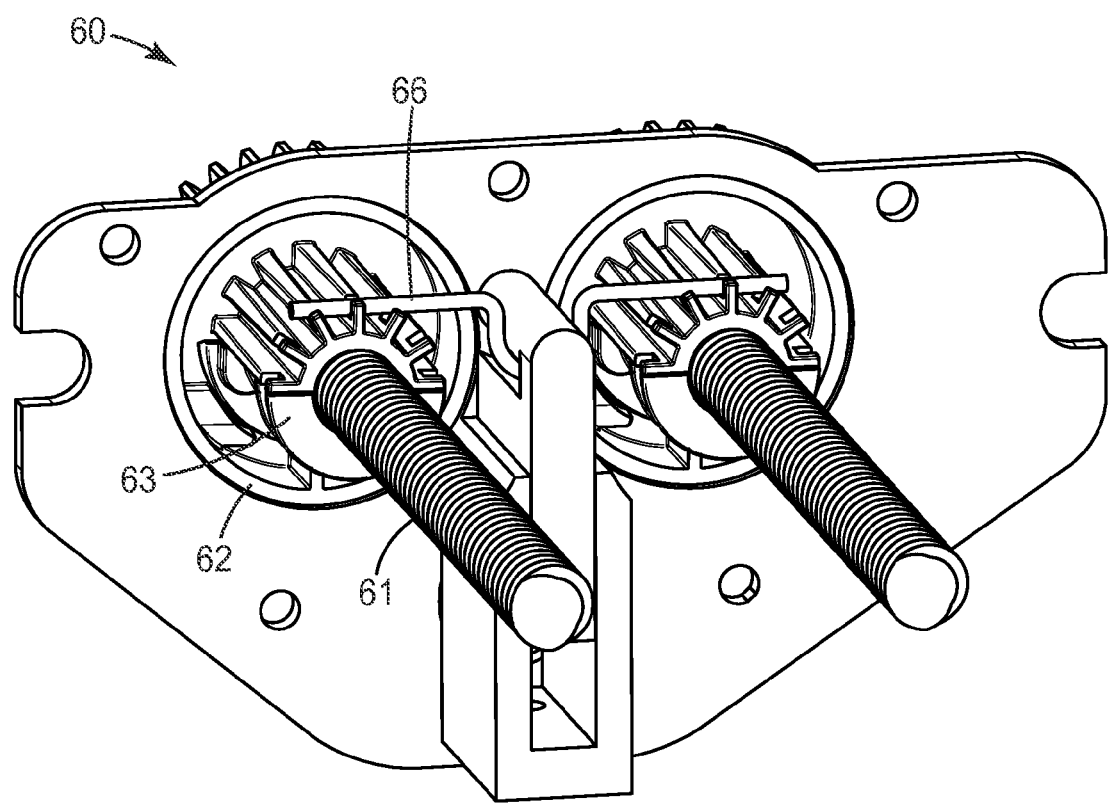
FIG. 9 is a perspective view of an assembly comprising two spindle drives according to a further embodiment of the invention.

FIG. 9 shows a spindle drive 60 having a link 62 cooperating with a spindle 61. The Figure shows a situation in which the link and the spindle are in an engaged position. In particular the link 62 has a nut 63 which is pivotable so that it is operable to engage or disengage with the spindle. The embodiment shown in FIG. 9 is similar to the embodiment shown in FIGS. 3*a*, 3*b*, but further has a spring 66 which by default urges the nut toward the engaged position. Therefore when used in a dispensing device the spindle drive may be normally in the engaged position so that material may be dispensed from the device by just switching the motor of the device on. The nut may be mechanically connected to an actuator (not shown) allowing the link to be disengaged from the spindle against spring force. Therefore a user may operate the actuator to disengage the link and the spindle from one another for quick displacement of the piston from or toward the compartments. Such an embodiment may be advantageous in that it may provide for relatively high forces for dispensing material because the spring force may support the self-locking function of the spindle drive. In an alternative embodiment the spring by default urges the spring toward the disengaged position. Operating the actuator may in this embodiment bring the link and the spindle in engagement with one another and preferably also may cause the motor to be switched on. For stopping dispensing the actuator may be released or operated again which preferably causes the motor to be switched off and the link and the spindle to disengage from one another. Thus the pistons are preferably released as the device is stopped so that pressure built up between the pistons and the compartments for dispensing can relieve. This may be advantageous because undesired afterflow of the materials when stopping dispensing may thus be prevented.

Figure 10:
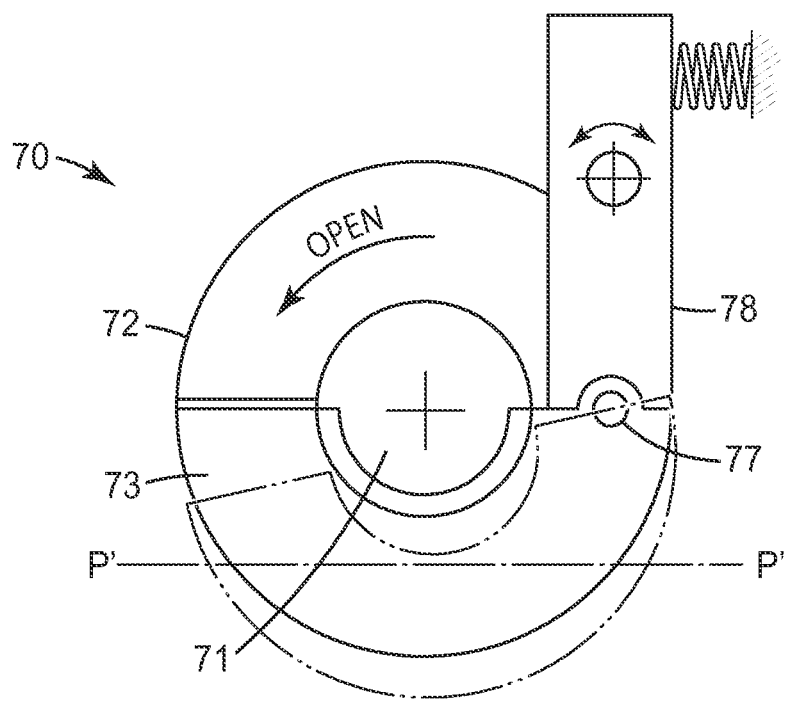
FIG. 10 is a schematic view of a link for cooperating with a spindle according to a further embodiment of the invention.

FIG. 10 illustrates an embodiment of a spindle drive 70 having a spindle 71 and a link 72. The link 72 has a nut 73 which is pivotally connected with the link 72 about a pivot axis P'. The link is rotatable about the spindle axis, but the nut is secured against rotation, in the example via a pin 77 that is retained by a lever 78. Therefore when the link 72 is rotated, in the Figure counterclockwise (see arrow), the nut is prevented from rotation and thus is forced to displace from the spindle radially (indicated by the dotted lines). A device using this embodiment may have axially stationary rotating spindles that drive axially movable links. Such links may be mechanically connected with pistons for advancing material. The skilled person will recognize that this drive principle reverses the drive principle in which the links are axially stationary and rotated to displace the spindles as described for other embodiments in this specification. Accordingly the embodiment of FIG. 10 may be combined or alternatively used with other embodiments described herein. In particular a spring for urging the nut or link towards the engaged or disengaged position by default may likewise be used for the embodiment of FIG. 10. Similar effects may be achieved by both drive principles although certain advantages may prevail or exclusively exist in one rather than the other principle.

Figure 11:
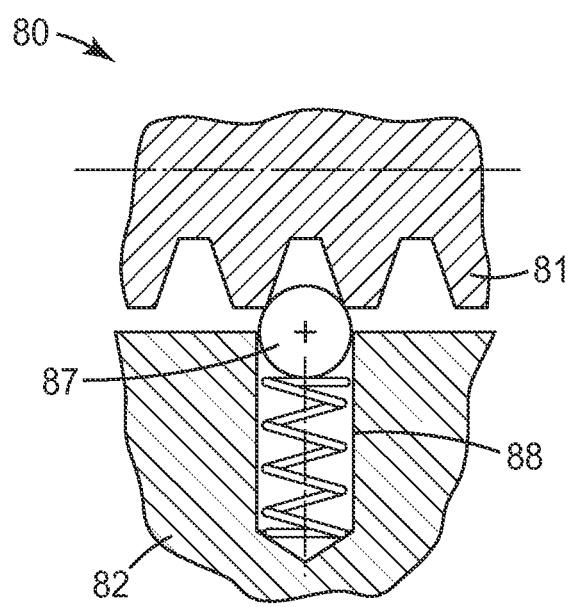
FIG. 11 is a cross-sectional view of a pitch finder according to an embodiment of the invention.

FIG. 11 shows a spindle drive 80 having a threaded spindle 81 and a link 82. A pitch finder 88 is arranged at the link which comprises a ball 87 which is resiliently urged toward the spindle 81. The ball 87 preferably is urged toward the spindle 81 in the disengaged position of the spindle drive. Therefore the link and the spindle in the disengaged position may be freely movable relative to one another. The pitch finder 88 may be adapted to snap between flanges of the spindle thread as the link and the spindle are moved relative to one another and thus may indicate preferred positions in which the link and the spindle may be engageable without substantial further axial movement relative to one another. For example a nut (not shown) having a corresponding thread for engaging with the spindle may in the indicated preferred positions engage smoothly with the spindle.

Figure 12:
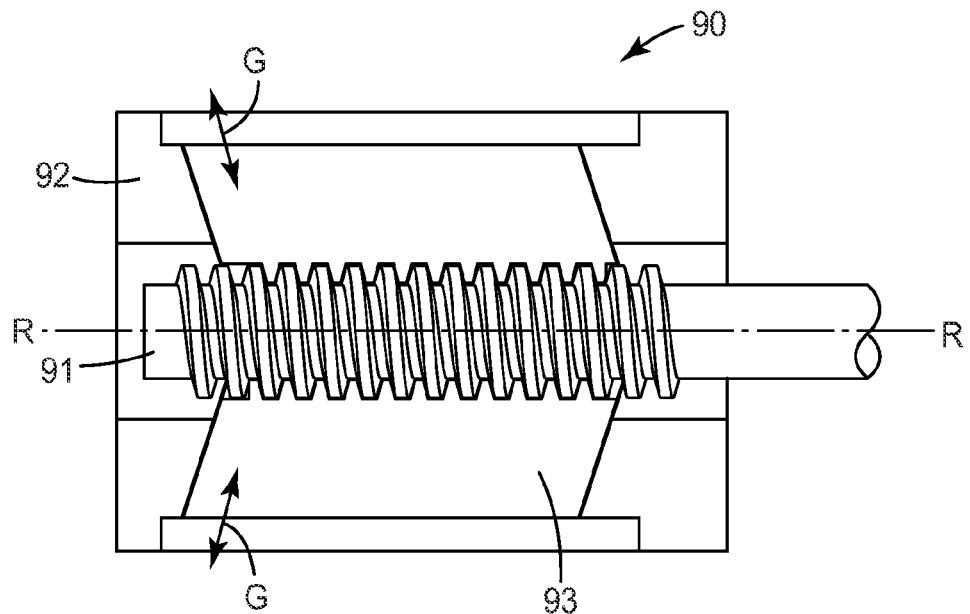
FIG. 12 is a perspective view of a spindle drive according to an embodiment of the invention.

FIG. 12 shows a spindle drive 90 having a threaded spindle 91 and a link 92. The link 92 comprises a threaded nut 93. The spindle 91 and the link 92 are adapted such that they can be disengaged or engaged with one another by a relative movement of the spindle 91 and the nut 93 laterally to a rotation axis R of the spindle. Therefore the nut 93 only partially surrounds the spindle 91, for example the nut 93 may comprise one or more threaded segments which surround about 180° of the spindle circumference or less. In the example the threaded nut 93 is guided for a movement generally laterally to the rotation axis R of the spindle 91 for controlling an engagement or a disengagement with the spindle 91. Further the nut 93 is preferably guided for a parallel motion. This means that the nut 93 is guided such that the angular orientation of the nut 93 is maintained generally constant during a movement of the nut 93 relative to the spindle 91. In particular the threaded nut 93 is guided for a movement in a guiding dimension G that is generally parallel to a flank angle ("A" indicated in FIG. 13) of the thread. The flank angle is measured in a plane aligned with the rotation axis. Further the flank angle is measured in that plane between the rotation axis and a surface of a flank of the thread. In the example the guidance in the guiding dimension G is provided by a linear guide, for example a sliding or roller linear guide.

Figure 13A:
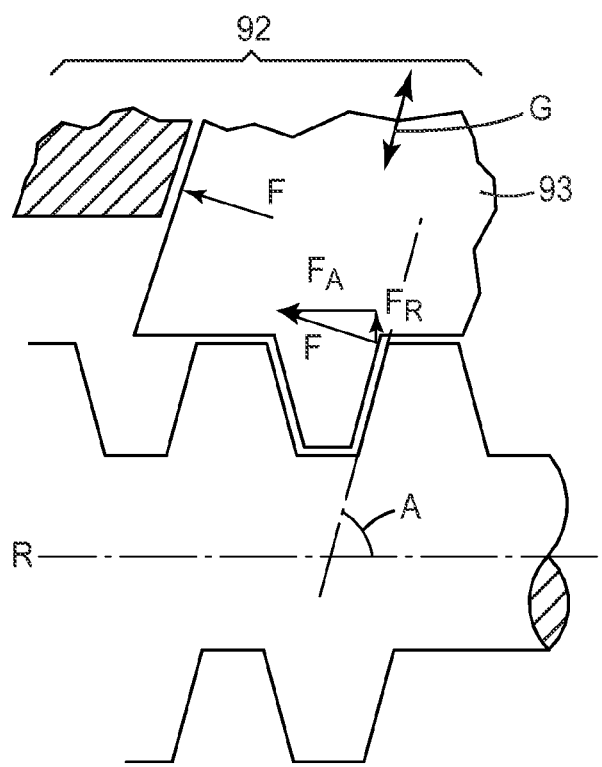
FIG. 13a, 13b are schematic views illustrating functions of the spindle drive of FIG. 12.

FIG. 13a schematically shows the spindle drive 90 with the spindle 91, the link 92, and the nut 93. In the example the spindle 91 may be driven for displacing the nut 93 toward the left in the Figure. A corresponding force triangle indicating an axial force $F_A$, a radial force $F_R$ and a resulting force F is illustrated. In case the spindle drive 90 is operated to transmit an axial force $F_A$ between the spindle 91 and the nut 92 the radial force $F_R$ occurs due to the thread having a thread angle A which is different from 90° relative to the rotation axis R of the spindle. The guidance of the nut 93 relative to the spindle 91 is however such that the guiding dimension G is oriented generally perpendicular to the resulting force F. Thus the resulting force F preferably cannot cause any force component in the dimension of the guiding dimension G so that urging of the nut 93 in the guiding dimension G is prevented. Therefore if the spindle drive 90 is driven for a displacement in one direction of the spindle 91 and the nut 93 relative to one another an automatic disengagement of the spindle 91 and the nut 93 (due to radial forces) is prevented.

Figure 13B:
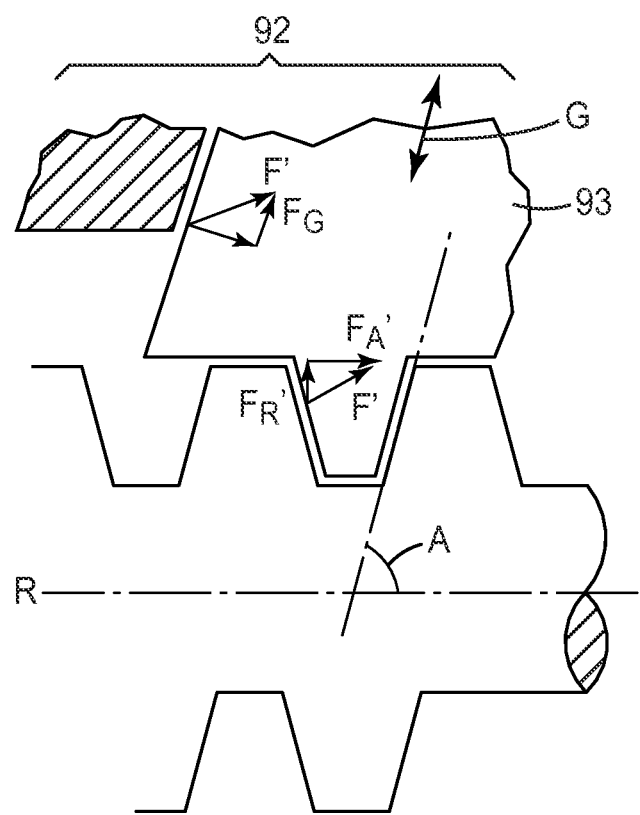

FIG. 13b illustrates the spindle drive 90 being driven in an opposite displacement direction relative to the direction illustrated in FIG. 13a. An axial force $F_{A'}$, a radial force $F_{R'}$ and a resulting force F' is indicated in the Figure. A force component $F_G$ is induced in the guiding dimension G so that the nut is urged in the guiding dimension away from the spindle. Therefore the nut 93 is caused to automatically disengage from the spindle in this displacement direction of the nut 93 and the spindle 91 relative to one another. Thus the spindle drive 90 may provide for transmitting relatively high forces in one axial direction, and may provide for automatically disengaging the nut 93 and the spindle 91 in the opposite direction.

Figure 14:
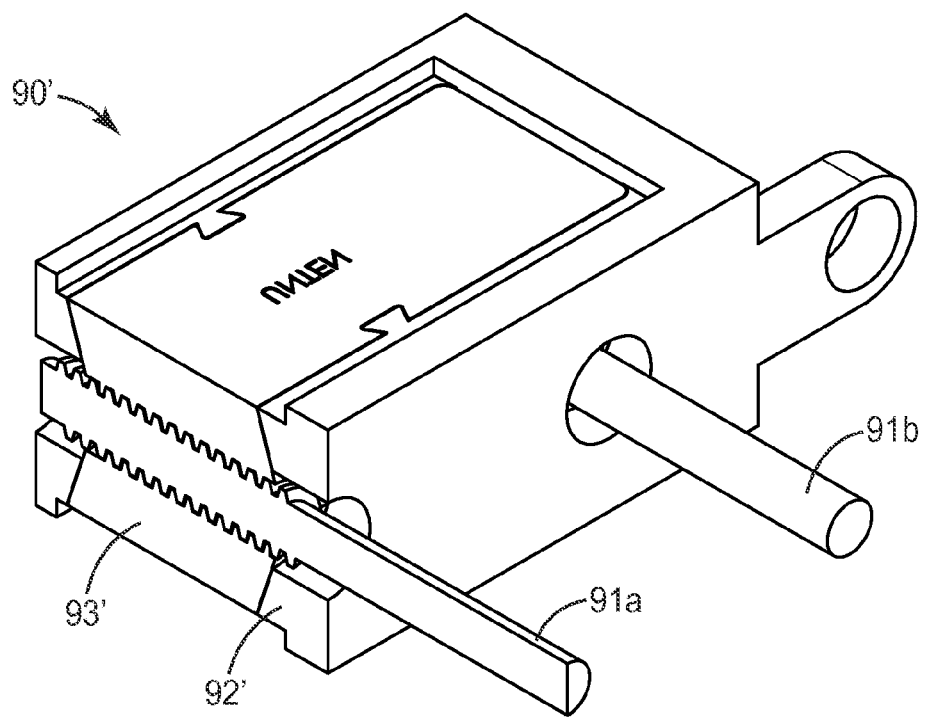
FIG. 14 is a perspective view of a spindle drive according to another embodiment of the invention.

FIG. 14 shows a spindle drive 90' which is similar to the spindle drive shown in FIGS. 12, 13 but having two threaded spindles 91a, 91b and a common link 92'. The spindles 91a 91b and the link 92' are adapted for disengageable engagement with one another. The link 92' further comprises a common nut 93' having two threads for engaging the threads of the two spindles 91a, 91b. The skilled person will recognize that two separate threaded nuts may be provided with the common link likewise.

Figure 15:
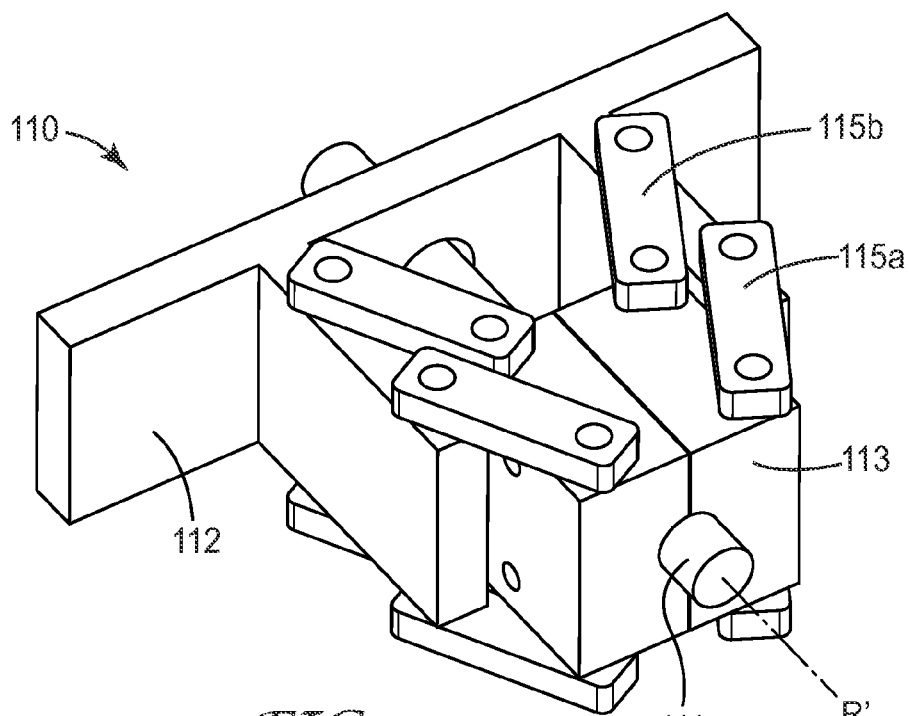
FIG. 15 is a perspective view of a spindle drive according to a further embodiment of the invention.

FIG. 15 shows an alternative spindle drive 110. The spindle drive 110 has a threaded spindle 111 and a link 112. The link 112 comprises a threaded nut 113 which is movable laterally to a rotation axis R' of the spindle 111. The thread of the nut 113 is engageable and disengageable from the thread of the spindle 111 by such a lateral movement. In the example two nuts in the form of two half sections are present which are separable for disengaging from the spindle 111 and which can be joined for engaging the spindle 111. Although two or more nuts may be present in the example the embodiment is further described referring to the nut 113 only. The nut 113 is guided for a parallel motion so that that the nut 113 is guided such that the angular orientation of the nut 113 is maintained generally constant during a movement of the nut 113 relative to the spindle 111. In the example the nut 113 is guided by a parallelogram guide which has pivotable levers 115a, 115b connecting the nut 113 and the link 112. Each of the levers has a pivot connection with the link and a further pivot connection with the nut. Thus a guide for parallel motion is provided. In the example the parallelogram guide has further two levers having pivot connections that are generally coaxial with the pivot connections of the levers 115a, 115b. Therefore the mechanical stability of the parallelogram guide may be maximized. A further nut may have a similar parallelogram guide, as illustrated.

Figure 16:
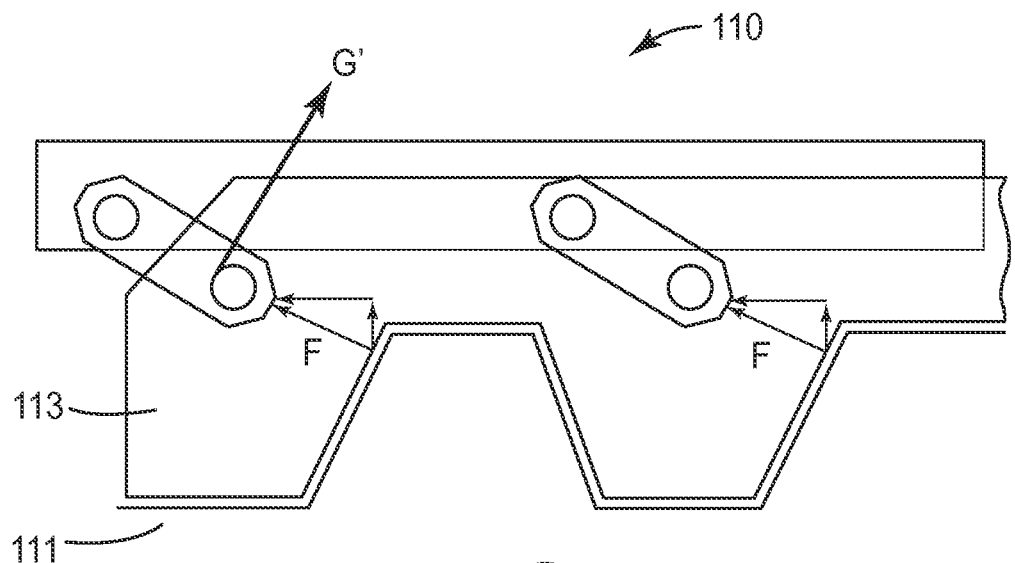
FIG. 16 is a perspective view of a spindle drive according to still another embodiment of the invention.

FIG. 16 illustrates a force triangle as it may result from an operation of the spindle drive 110 for displacing the nut 113 and the spindle in one direction relative to one another. The parallelogram guide is adapted to guide the nut 93 for a movement on a guiding circle. However in the engaged position of the nut 113 and the spindle 111 the parallelogram guides the nut 93 for a movement in a guiding direction G'

(which is a tangent on the guiding circle in the position shown). As described in FIG. 13a the resulting force F is directed generally perpendicular to the guiding direction G'. Thus the force F cannot cause a force component in the guiding direction G'. Consequently also this embodiment allows for preventing the nut 113 to automatically disengage from the spindle 111 in one displacement direction, but provides for disengaging the nut 113 from the spindle 111 in the opposite displacement direction of the spindle 111 and the nut 113 relative to one another.

Figure 17:
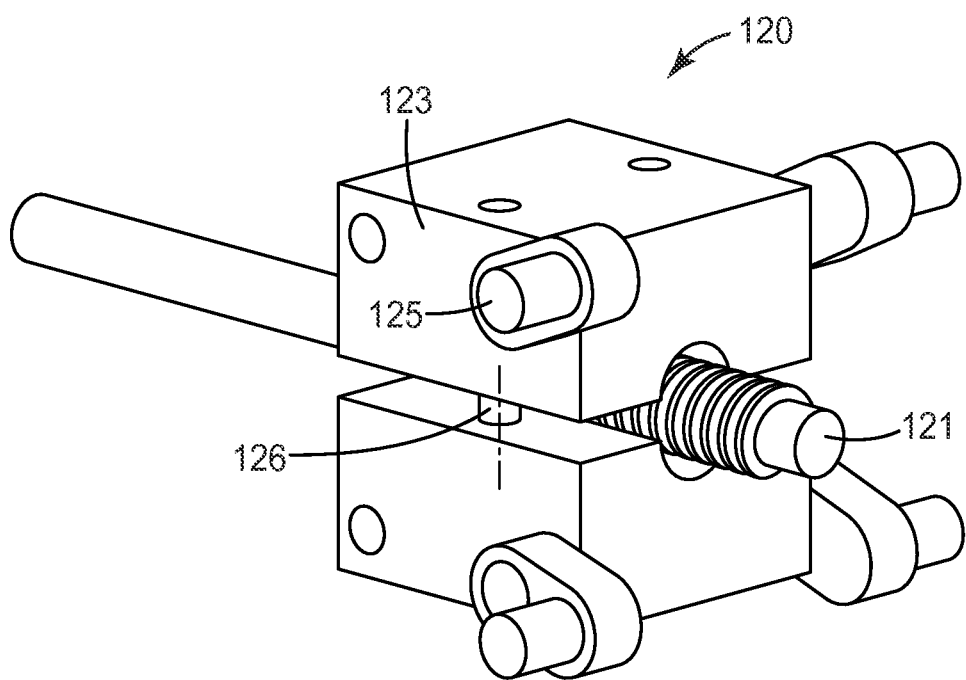
FIG. 17 is a perspective view of a further spindle drive according to an embodiment of the invention.

FIG. 17 illustrates a spindle drive 120 in which a lever 125 and a linear guide 126 are used in combination to provide guidance for parallel motion of a nut 123 relative to a spindle 121. The example operates similarly to the examples illustrated in FIGS. 15 and 16. The skilled person will recognize further embodiments providing for guidance of a nut and a spindle for a parallel motion relative to one another. Such an embodiment may be advantageous in that it preferably provides a self-maintaining engagement of the nut and the spindle when the spindle drive is operated in one displacement direction of the nut and the spindle relative to one another. Further such an embodiment preferably provides an automatic disengagement of the nut and the spindle when the spindle drive is operated in the opposite displacement direction of the nut and the spindle relative to one another.

The invention claimed is:

1. A device for dispensing a dental material, comprising at least one compartment for receiving the dental material, at least one piston for extruding the dental material from the compartment and a spindle drive for moving the piston and the compartment relative to one another, the spindle drive comprising a spindle and a link which are adapted for disengageable engagement with one another, wherein the spindle and the link are operable relative to each other between an engaged position in which the link and the spindle are engaged with one another, and a disengaged position in which the spindle and the link are disengaged from one another; wherein the link and the spindle in the engaged position are rotatable relative to each other about a rotation axis; wherein the link comprises a nut; wherein the nut is guided for a parallel motion relative to the spindle in a guiding direction that is non-parallel and non-perpendicular to the rotation axis of the spindle; wherein the nut is threaded; and wherein the guiding direction is generally parallel to a flank angle of a thread of the nut.

2. The device of claim 1, wherein the spindle and the link are adapted to displace relative to each other axially to the rotation axis.

3. The device of claim 2, wherein the displacement between the spindle and the link provides for a displacement between the piston and the compartment for extruding the dental material.

4. The device of claim 1, wherein the spindle is threaded and the link has an engagement structure for engaging the spindle thread.

5. The device of claim 4, wherein the nut carries the engagement structure.

6. The device of claim 5, wherein the engagement structure is arranged at a section of the nut which only partially surrounds the spindle.

7. The device of claim 5, wherein the relative movement between the spindle and the nut is provided by the nut being pivotable relative to the spindle about a pivot axis which extends generally transverse to the rotation axis, and wherein the nut is adapted such that the engagement structure is radially offset from the pivot axis.

8. The device of claim 7, wherein the pivot axis is arranged outside an outer perimeter or outside the effective diameter of the spindle thread, and wherein the engagement structure is arranged in a radius from the pivot axis, with the radius being greater than the distance between the pivot axis and the outer perimeter or outside the effective diameter of the spindle thread.

9. The device of claim 4, in which the spindle and the nut are urged in the engaged or in the disengaged position by spring load.

10. The device of claim 9, having a cam which is operable for retaining the nut in the engaged position against the spring load, and for releasing the nut so that it can move toward the disengaged position by spring load.

11. The device of claim 9, in which the nut is connected to an actuator allowing for moving the nut toward the disengaged position against spring load.

12. The device of claim 11, having two plungers, two compartments and two pistons, and further being adapted to mix components received in the compartments to form the dental material.

13. The device of claim 12, comprising two spindle drives each comprising a spindle and a link wherein the links are rotatably interconnected so that rotation of one causes rotation of the other one.

14. The device of claim 1, wherein the spindle is axially movable in the device and the link is axially fixed in the device.

15. The device of claim 1 having at least one plunger carrying the piston.

16. The device of claim 1, wherein the nut is guided in the guiding direction that is non-parallel and non-perpendicular to the rotation axis of the spindle, such that when the spindle drive is driven for a displacement in one direction of the spindle and the nut relative to one another, an automatic disengagement of the spindle and the nut is prevented, and when the spindle drive is driven in the opposite direction, the nut is caused to automatically disengage from the spindle.

17. The device of claim 1, wherein the nut is guided for a parallel motion relative to the spindle in a guiding direction that is non-parallel and non-perpendicular to the rotation axis of the spindle, such that an angular orientation of the nut is maintained generally constant during a movement of the nut and the spindle relative to one another.

18. A device for dispensing a dental material, comprising at least one compartment for receiving the dental material, at least one piston for extruding the dental material from the compartment and a spindle drive for moving the piston and the compartment relative to one another, the spindle drive comprising a spindle and a link which are adapted for disengageable engagement with one another, wherein the spindle and the link are operable relative to each other between an engaged position in which the link and the spindle are engaged with one another, and a disengaged position in which the spindle and the link are disengaged from one another; wherein the link comprises a nut; wherein the nut is guided for a parallel motion relative to the spindle in a guiding direction that is non-parallel and non-perpendicular to the rotation axis of the spindle, such that when the spindle drive is driven for a displacement in one direction of the spindle and the nut relative to one another, an automatic disengagement of the spindle and the nut is prevented, and when the spindle drive is driven in the opposite direction, the nut is caused to automatically disengage from the spindle.

* * * * *